United States Patent [19]

Kelly

[11] Patent Number: 5,851,427
[45] Date of Patent: *Dec. 22, 1998

[54] PHOTOCROSS-LINKABLE NAPHTHYL DERIVATIVES

[75] Inventor: Stephen Kelly, Beverley, England

[73] Assignee: Rolic AG, Zug, Switzerland

[*] Notice: The term of this patent shall not extend beyond the expiration date of Pat. No. 5,700,393.

[21] Appl. No.: 606,102

[22] Filed: Feb. 23, 1996

[30] Foreign Application Priority Data

Mar. 3, 1995 [CH] Switzerland ............................. 607/95

[51] Int. Cl.$^6$ .......................... C09K 19/32; C09K 19/52; C07C 69/76; C07D 303/12
[52] U.S. Cl. .............................. 252/299.62; 252/299.01; 252/299.6; 252/299.61; 252/299.63; 549/557; 549/369; 549/370; 560/100; 560/102; 560/108; 560/60; 568/626; 544/298; 546/339; 546/340
[58] Field of Search .......................... 252/299.62, 299.6, 252/299.61, 299.01, 299.63, 299.66; 560/100, 102, 108, 60; 585/25; 544/298; 546/399, 340; 549/369, 370, 560, 557; 556/428, 437; 568/626, 647

[56] References Cited

U.S. PATENT DOCUMENTS

| | | | |
|---|---|---|---|
| 4,440,945 | 4/1984 | Conciatori et al. | 560/86 |
| 4,801,734 | 1/1989 | Kock et al. | 560/73 |
| 4,983,479 | 1/1991 | Broer et al. | 430/20 |
| 5,182,394 | 1/1993 | Kim | 549/557 |
| 5,230,828 | 7/1993 | Kelly | 252/299.62 |
| 5,237,076 | 8/1993 | Mallon et al. | 549/562 |
| 5,411,676 | 5/1995 | Kelly et al. | 252/299.63 |

FOREIGN PATENT DOCUMENTS

| | | |
|---|---|---|
| 331 233 | 2/1989 | European Pat. Off. . |
| 0 449 049 A2 | 10/1991 | European Pat. Off. . |
| 689 065 | 12/1995 | European Pat. Off. . |
| 689 084 | 12/1995 | European Pat. Off. . |
| 195 17 762 A1 | 11/1995 | Germany . |
| 1-118802 | 5/1989 | Japan . |

OTHER PUBLICATIONS

Derwent Abstract No. 96–041726/05.
Derwent Abstract No. 96–041741/05.
Melissaris, et al: "High Modulus and High Tg Thermally Stable Polymers from Di–p–ethynylbenzoyl Ester Monomers: Synthesis, Solid State Polymerization; Processing, and Thermal Properties" Macromolecules vol. 27 (10); pp. 2675–2684, (1994).

Primary Examiner—Cynthia Harris Kelly
Attorney, Agent, or Firm—Bryan Cave LLP

[57] ABSTRACT

Photocross-linkable naphthyl derivatives include compounds of the formula:

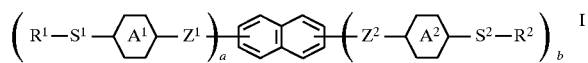

wherein $R^1$ and $R^2$ each independently signify a cross-linkable group;

$S^1$ and $S^2$ signify —$(CY_2)_m$-, —$O(CY_2)_m$-, —$(CY_2)_mO$—, —$(CY_2)_mCOO$—, —$(CY_2)_mOOC$—, —$(Si[(CH_3)_2]O)_m$-, —$OCH_2(Si[(CH_3)_2]O)_mSi[(CH_3)_2]CH_2O$— or —$NHCH_2(Si[(CH_3)_2]O)_mSi[(CH_3)_2]CH_2NH$—;

Y signifies hydrogen, fluorine or methyl;

a signifies 0 or 1;

b signifies 1 or 2, with the proviso that a+b=2;

m signifies a whole number of 1 to 16;

$A^1$ and $A^2$ each independently signify 1,4-phenylene, which is optionally mono- or multiply-substituted with halogen, cyano, methyl, methoxy and/or acetyl, pyridine-2,5-diyl, pyrimidine-2,5-diyl, trans-1,4-cyclohexylene or trans-1,3-dioxane-2,5-diyl; and $Z^1$ and $Z^2$ each independently signify a single bond, —$CH_2CH_2$—, —$OCH_2$—, —$CH_2O$—, —$COO$—, —$OOC$—, —$(CH_2)_4$—, —$O(CH_2)_3$— or —$(CH_2)_3O$—, liquid crystalline mixtures which contain such compounds, and their use in the cross-linked state for optical components.

30 Claims, No Drawings

PHOTOCROSS-LINKABLE NAPHTHYL DERIVATIVES

BACKGROUND OF THE INVENTION

1. Field

The present invention is concerned with photocross-linkable naphthyl derivative compounds, mixtures which contain such compounds, and the use of such compounds and mixtures in the cross-linked state for optical components.

2. Description

Liquid crystals having at least two photochemically oligomerizable or polymerizable groups can be orientated on a substrate or in a cell, such as by orientating in layers or in a field. These orientated liquid crystals, when provided with a suitable amount of a photoinitiator, can be polymerized by irradiation with light of a suitable wavelength. The cross-linked structure thereby produced is stable even at high temperatures. Such layers can be, for example, parts of hybrid layers, as are described in European Patent Applications EP-A-0 689 084 and EP-A-0 689 065, corresponding to U.S. application Ser. Nos. 08/489,865 and 08/489,866, both abandoned, the contents of which are herein incorporated by reference. Thus, optical components such as, retarders, wave guides, optical grids and filters, integrated color filters, cells having piezoelectric properties, and cells having non-linear optical ("NLO") properties, can be produced. Such optical components can be used, for example, in projection systems.

Further properties, such as birefringence, refractive index, transparency and the like, must fulfill different requirements depending on the intended field of use. For example, materials for optical retarders should have a high birefringence in order to minimize layer thickness of the integrated optical component.

In addition to the general interest in photocross-linkable liquid crystals for optical components, such liquid crystalline materials are suitable as cladding for glass fibers used in optical data transmission. The use of such materials increases the elastic modulus in the longitudinal axis of the fiber, reduces thermal expansion coefficient, and avoids microdistortion losses, thereby increasing mechanical stability.

Photocross-linkable liquid crystals should have good chemical and thermal stability, good solubility in common solvents, and good stability in electric fields and electromagnetic radiation. Furthermore, photocross-linkable liquid crystals should have a suitable mesophase of from about 25° C. to about 80° C., and if possible from about 25° C. to about 100° C., (for example a broad smectic or nematic mesophase or a chiral smectic or cholesteric mesophase, for the applications referred to above).

Since liquid crystals are usually used in mixtures of several components, it is important that the components have a good miscibility with one another. Conventional photo-chemically oligomerizable or polymerizable liquid crystals usually have a high melting point and clearing point which disadvantageously can lead to premature spontaneous, thermal polymerization during processing. Typically, processing is carried out at temperatures just below the clearing point, because viscosity is lowest at these temperatures and thus most favorable for good orientability. Spontaneous polymerization leads to the formation of domains in which the optical and thermal properties in the cross-linked layers are clearly influenced. Although melting point can be decreased by the production of complicated mixtures having several components (therefore allowing lower temperature processing), such processing unfortunately brings with it the danger of a crystallization of the conventional polymerizable liquid crystals. Photochemically oligomerizable or polymerizable compounds are described, for example, in EP-A-0 331 233, corresponding to U.S. Pat. No. 4,983,479, the contents of which are herein incorporated by reference.

Accordingly, there is a need (especially in the context of optical filters) for photochemically oligomerizable or polymerizable compounds which have a high optical anisotropy and low melting points and clearing points to permit ready processing at temperatures above room temperature in both the liquid crystalline state and in solution. Further, such compounds should be orientable and structurable as domain-free as possible, and should have excellent thermal stability and long-term stability in the cross-linked state.

SUMMARY OF THE INVENTION

The subject invention provides a compound of the formula:

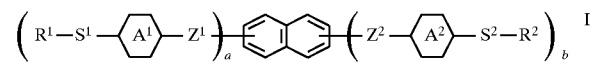

wherein $R^1$ and $R^2$ each independently is a cross-linkable group;

$S^1$ and $S^2$ each independently is —$(CY_2)_m$-, —$O(CY_2)_m$-, —$(CY_2)_mO$—, —$(CY_2)_mCOO$—, —$(CY_2)_mOOC$—, —$(Si[(CH_3)_2]O)_m$-, —$OCH_2(Si[(CH_3)_2]O)_mSi[(CH_3)_2]CH_2O$—, or —$NHCH_2(Si[(CH_3)_2]O)_mSi[(CH_3)_2]CH_2NH$—;

Y is hydrogen, fluorine, or methyl;

a is 0 or 1;

b is 1 or 2, and a+b=2;

m is a whole number of from 1 to 16;

$A^1$ and $A^2$ each independently is pyridine-2,5-diyl, pyrimidine-2,5-diyl, trans-1,4-cyclohexylene, trans-1,3-dioxane-2,5-diyl, or 1,4-phenylene which is unsubstituted, mono-substituted or multiply-substituted with one or more substituents selected from the group consisting of halogen, cyano, methyl, methoxy, and acetyl; and $Z^1$ and $Z^2$ each independently is a single bond, —$CH_2CH_2$—, —$OCH_2$—, —$CH_2O$—, —$COO$—, —$OOC$—, —$(CH_2)_4$—, —$O(CH_2)_3$—, or —$(CH_2)_3O$—.

DETAILED DESCRIPTION OF THE INVENTION

The present invention will now be described in terms of its preferred embodiments. These embodiments are provided to aid in understanding the invention, but are not to be construed as limiting.

The present invention provides compounds which are outstandingly suitable as single components or as components of liquid crystal mixtures for optical components, namely compounds of the formula

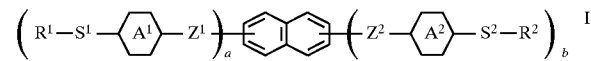

wherein $R^1$ and $R^2$ each independently signify a cross-linkable group such as ethylene, acrylate, methacrylate, 2-chloroacrylate, 2-phenylacrylate, acryloylphenylene, acrylamide, methacrylamide, 2-chloroacrylamide, 2-phenylacrylamide, epoxy, itaconic acid ester, vinyloxy, vinyl ester, styrene derivative, siloxane, ethyleneimine derivative, maleic acid derivative, fumaric acid derivative or a cinnamic acid derivative, which is optionally substituted with methyl, methoxy, cyano and/or halogen;

$S^1$ and $S^2$ signify —$(CY_2)_m$-, —$O(CY_2)_m$-, —$(CY_2)_mO$—, —$(CY_2)_mCOO$—, —$(CY_2)_mOOC$—, —$(Si[(CH_3)_2]O)_m$-, —$OCH_2(Si[(CH_3)_2]O)_mSi[(CH_3)_2]CH_2O$— or —$NHCH_2(Si[(CH_3)_2]O)_mSi[(CH_3)_2]CH_2NH$—;

Y signifies hydrogen, fluorine or methyl;

a signifies 0 or 1;

b signifies 1 or 2, with the proviso that a+b=2;

m signifies a whole number of 1 to 16;

$A^1$ and $A^2$ each independently signify 1,4-phenylene, which is optionally mono- or multiply-substituted with halogen, cyano, methyl, methoxy and/or acetyl, pyridine-2,5-diyl, pyrimidine-2,5-diyl, trans-1,4-cyclohexylene or trans-1,3-dioxane-2,5-diyl; and $Z^1$ and $Z^2$ each independently signify a single bond, —$CH_2CH_2$—, —$OCH_2$—, —$CH_2O$—, —$COO$—, —$OOC$—, —$(CH_2)_4$—, —$O(CH_2)_3$— or —$(CH_2)_3O$—.

The term "cross-linkable group" as used herein has the significance which is generally recognized the art. Cross-linkable groups are functional groups for the preparation of networks. For example, cross-linkable groups include polymerizable groups, such as acrylate and the like, as well as dimerizable groups, such as cinnamic acid and its derivatives. The scope of the term "cross-linkable group" is readily apparent to the skilled artisan having read the present specification.

The compounds of formula I are distinguished by their relatively low viscosity. They can accordingly be applied without problems to a suitable surface. This generally takes place by spin-coating. Since, moreover, the compounds in accordance with the invention have a liquid crystalline phase they can be directed prior to the cross-linking by the application of an electric field.

The term "1,4-phenylene, which is mono- or multiply-substituted with halogen, cyano, methyl, methoxy and/or acetyl," embraces in the scope of the present invention 1,4-phenylene, 1,4-phenylene substituted with fluorine, bromine, chlorine, cyano, methyl, methoxy or acetyl, such as, for example 2- or 3-fluoro-1,4-phenylene, 2,3-, 2,6- or 3,5-difluoro-1,4-phenylene, 2- or 3-chloro-1,4-phenylene, 2,3-, 2,6- or 3,5-dichloro-1,4-phenylene, 2- or 3-bromo-1,4-phenylene, 2- or 3-cyano-1,4-phenylene, 2,3-dicyano-1,4-phenylene, 2- or 3-acetyl-1,4-phenylene, 2- or 3-methyl-1,4-phenylene, 2- or 3-methoxy-1,4-phenylene, and the like. Especially preferred compounds of formula I are those in which rings $A^1$ and $A^2$ are the same and signify 1,4-phenylene or 2- or 3-fluoro-1,4-phenylene.

The spacer groups $S^1$ and $S^2$ can also be chiral, if desired. Preferred compounds of formula I are those in which $S^1$ and $S^2$ have the same significance. Preferred spacer groups are those in which Y signifies hydrogen and m is a whole number of 4 to 12.

Preferred residues $R^1$ and $R^2$ are acrylate, methacrylate, 2-chloroacrylate, 2-phenylacrylate, acryloylphenylene, acrylamide, methacrylamide, 2-phenylacrylamide, epoxy, vinyloxy, vinyl ester, styrene derivatives, maleic acid derivatives, fumaric acid derivatives and the like. It is these residues which can be cross-linked photochemically after coating the suitable carrier with compounds of formula I. In particular, there are preferred those compounds of formula I in which the residues $R^1$ and $R^2$ have the same significance. They preferably signify acrylate, methacrylate, 2-chloroacrylate, 2-phenylacrylate, vinyloxy or epoxy.

Especially preferred compounds of formula I are those in which the naphthyl ring is linked in position 1 and 5 or in position 1 and 4 with $Z^1$ and $Z^2$, especially those in which $Z^1$ and $Z^2$ are the same and signify —$OCH_2$—, —$CH_2O$—, —$COO$— or —$OOC$—.

Compounds which are especially preferred are those of the formulas

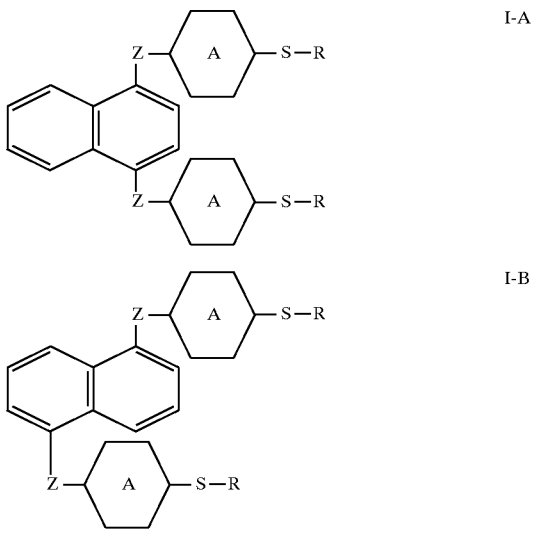

wherein

R signifies acrylate, methacrylate, 2-chloroacrylate, 2-phenylacrylate, vinyloxy or epoxy;

S signifies —$(CH_2)_{m'}$-, —$O(CH_2)_{m'}$- or —$(CH_2)_{m'}O$—;

m' is a whole number of 4 to 12;

A signifies 1,4-phenylene or 2- or 3-fluoro-1,4-phenylene; and

Z signifies —$OCH_2$— or —$OOC$—.

The compounds of formula I are very readily accessible synthetically. Thus, for example, compounds in which Z signifies a group —$OOC$— can be produced from 4-[ω-acryloxyalkyloxy]benzoic acids and the corresponding naphthohydroquinone (see Schemes 1 and 2). The esterification can be effected in a manner known per se. A preferred method comprises reacting the naphthohydroquinone with the carboxylic acid in a polar, but inert organic solvent (e.g. in dimethylformamide (DMF) or a halogenated hydrocarbon such as dichloromethane) in the presence of 4-(dimethylamino)pyridine (DMAP) and N,N'-dicyclohexylcarbodiimide (DCC). The 4-[ω-acryloxyalkyloxy]-benzoic acids are known per se and can be prepared by alkylating 4-hydroxybenzoic acid in the presence of a strong base and an w-halogenated alcohol as well as potassium iodide and subsequently esterifying the 4-[ω-hydroxyalkyloxy]benzoic acids with acrylic acid in the presence of p-toluenesulphonic acid (PTA).

The symbols used in the Schemes have the aforementioned significances.

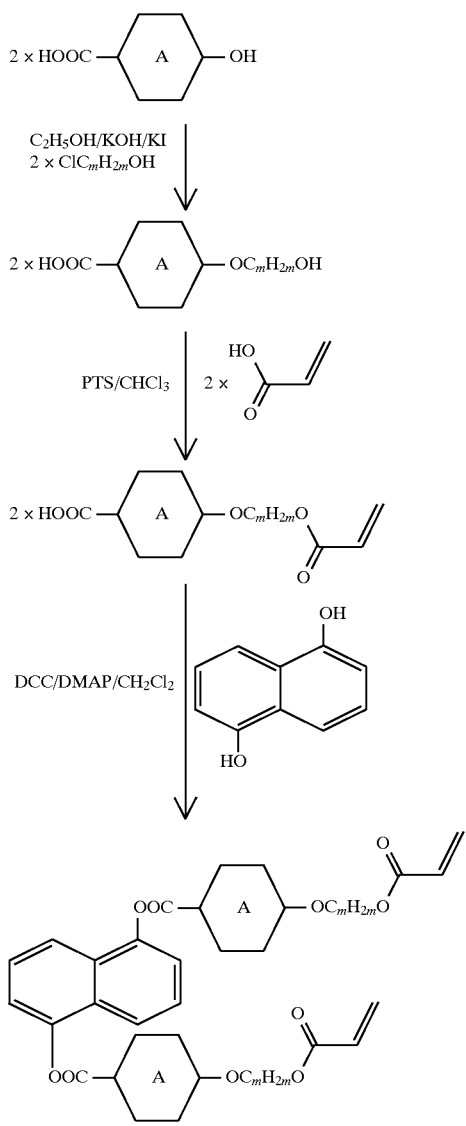

Scheme 1

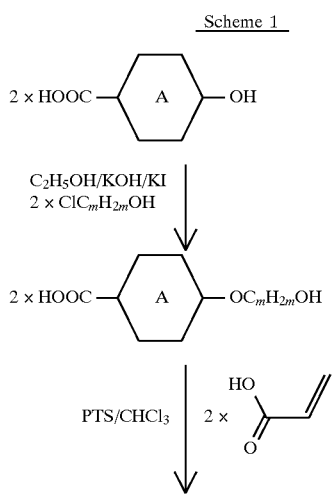

Scheme 1

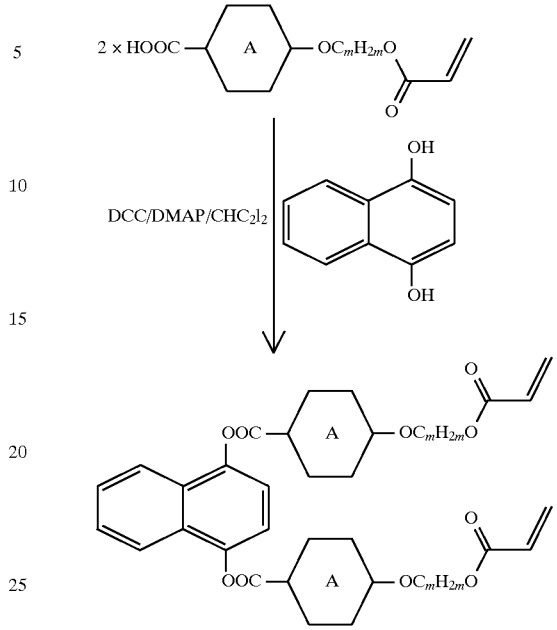

-continued
Scheme 1

A small amount of BHT (2,6-di-tert.-butyl-4-methyl-phenol/"butylhydroxytoluene") is admixed in each step in order to stop undesired thermal cross-linkage.

1,4-Bis(4-[ω-acryloyloxyalkyloxy]phenylmethylenoxy)-naphthalene derivatives, i.e. compounds of formula I in which Z signifies the group —$OCH_2$—, can be produced in a manner known per se by etherifying the corresponding 1,4-naphthohydroquinone with 4-[ω-acryloyloxyalkyloxy)] benzyl alcohols. The reaction can be effected, for example, in the presence of a dialkyl azodicarboxylate and triphenylphosphine. The 4-[ω-acryloyloxyalkyloxy)]benzyl alcohols used as the educt can be prepared by reducing the reaction product of acrylic acid with 4-[ω-hydroxyalkyloxy)]benzyl aldehydes. The 4-[ω-hydroxyalkyloxy)]benzaldehydes can be prepared by etherifying 4-hydroxybenzaldehyde with w-hydroxyalkyl halides in the presence of usual bases.

The compounds of formula I can be used as single compounds or in the form of mixtures with one another and/or with other liquid crystal components.

The liquid crystalline mixtures in accordance with the invention contain at least 2 components, of which at least one component is a compound of formula I. A second component and any other components can be additional compounds of formula I or other known liquid crystalline compounds with or without photocross-linkable groups. One or more chiral components can also be present in the mixture.

Having regard to the good solubility of the compounds of formula I and having regard to their good miscibility with one another, the content of different compounds of formula I in the mixtures in accordance with the invention can be high and can amount to about 100 wt. %.

The mixtures in accordance with the invention preferably contain, in addition to one or more compounds of formula I, one or more compounds from the group of compounds of the general formulas

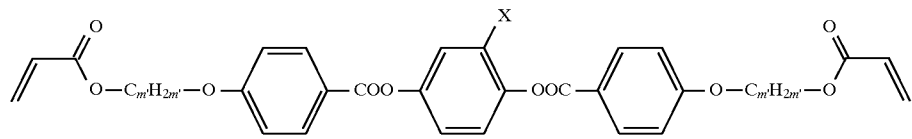
II
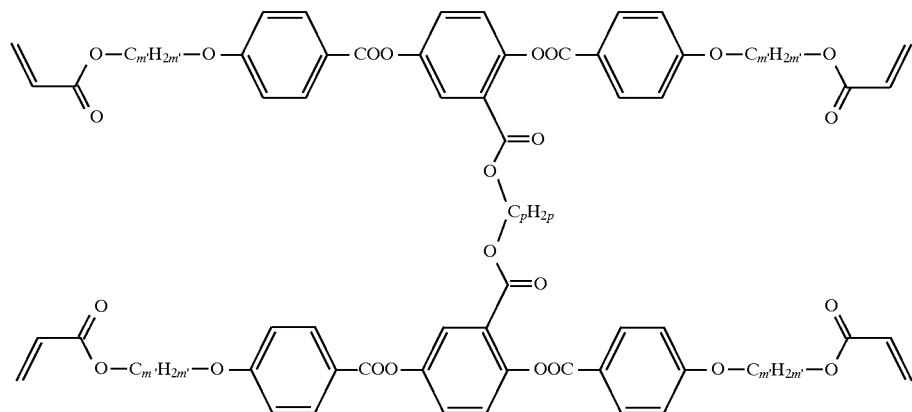
III
IV
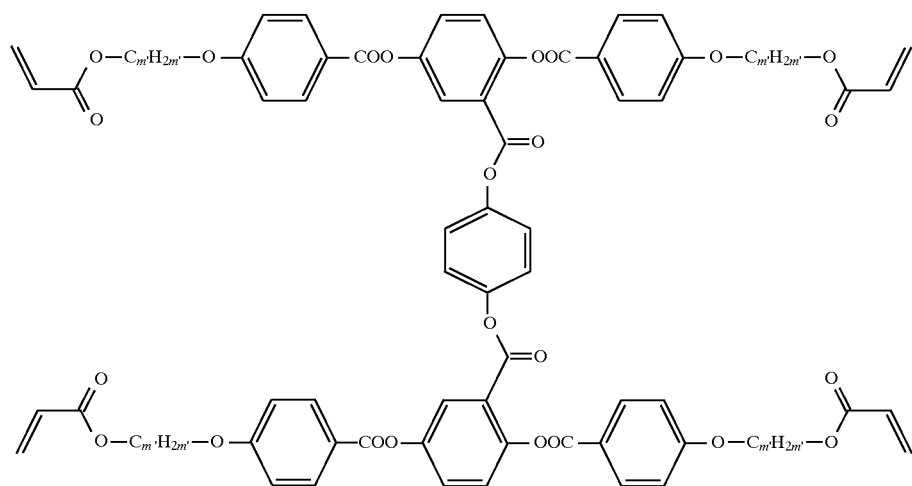
V
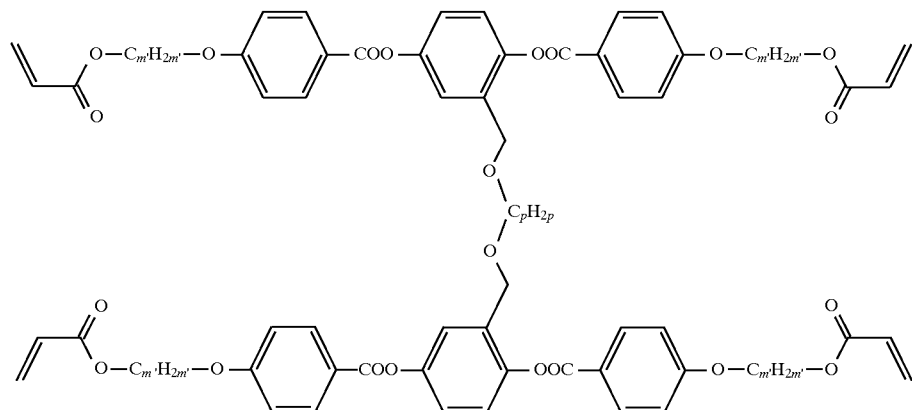

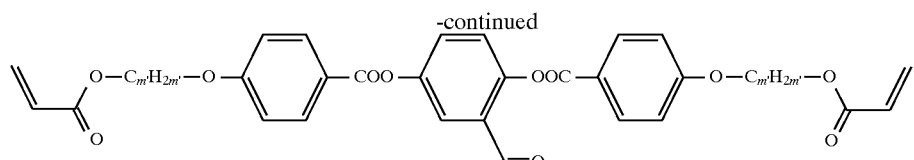

VI

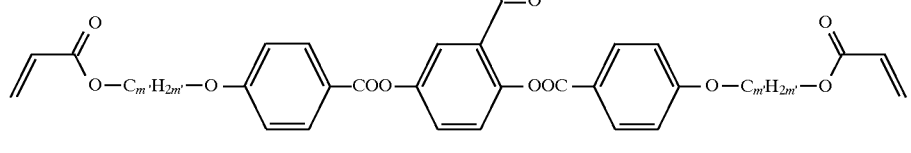

VII

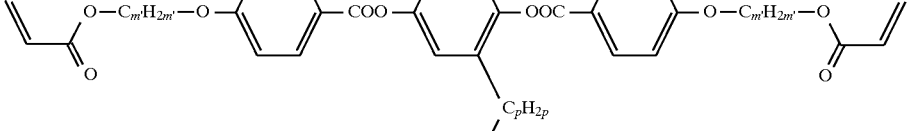

VIII

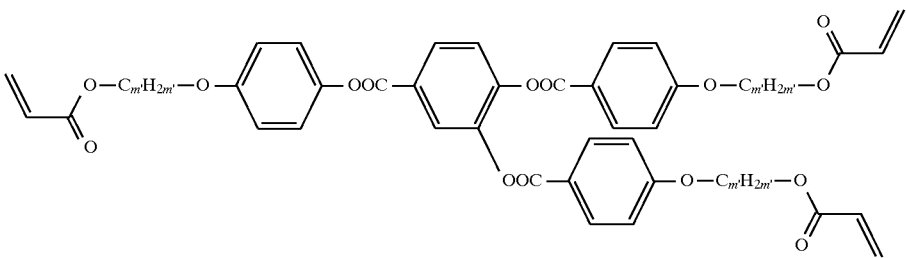

IX

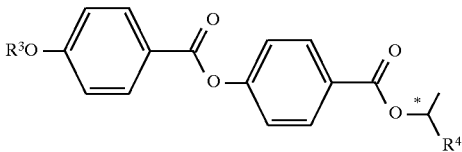

X

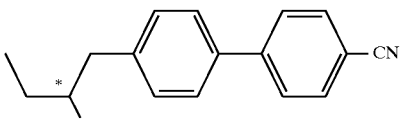

XI

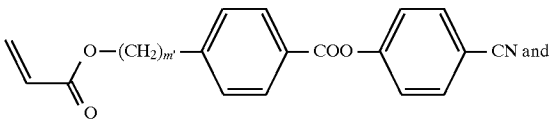

and

XII

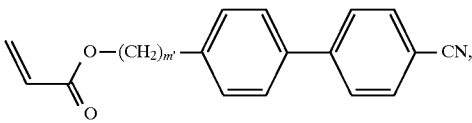

wherein
p signifies a whole number of 2 to 12;
$R^3$ and $R^4$ each independently signify alkyl or alkenyl with 2 to 12 carbon atoms;
X signifies hydrogen, lower alkyl, fluorine, bromine, chlorine or cyano;
m' signifies a whole number of 4 to 12; and
\* signifies a center of chirality.

"Lower alky" in connection with the compounds of formula II embraces methyl, ethyl, propyl, i-propyl, butyl, i-butyl, and tert.-butyl.

The production of the compounds of formula I and of liquid crystalline mixtures containing these compounds is illustrated in more detail by the following Examples. C signifies a crystalline phase, S signifies a smectic phase, N signifies a nematic phase and I signifies the isotropic phase.

All experiments in the following Examples were actually performed except for Examples 2 and 3.

EXAMPLE 1

0.8 g of N,N'-dicyclohexylcarbodiimide (DCC) was added at room temperature while stirring to a solution of 1.25 g of 4-[8-acryloyloxyoctyloxy)]benzoic acid, 0.25 g of 1,4-naphtho-hydroquinone and 0.2 g of 4-dimethylaminopyridine (DMAP) in 20 ml of dichloromethane. The reaction mixture was stirred at room temperature overnight, poured into 100 ml of water and then extracted three times with 50 ml of dichloromethane each time. The organic phases were combined, washed twice with 100 ml of water each time, dried over magnesium sulfate, filtered and the filtrate was subsequently concentrated. Chromatographic purification of the residue on silica gel with cyclohexane/ethyl acetate (vol. 8:2) and two-fold recrystallization from ethyl alcohol of the fractions which were pure according to thin-layer chromatography gave 0.2 g of 1,4-bis(4-[8-acryloyloxyoctyloxy]phenylcarbonyloxy)naphthalene; m.p. (C—N) 94° C., cl.p. (N—I) 104° C.

The following compounds can be prepared in an analogous manner:

1,4-Bis(4-[3-acryloyloxypropyloxy]phenylcarbonyloxy) naphthalene;
1,4-bis(4-[4-acryloyloxybutyloxy]phenylcarbonyloxy) naphthalene;
1,4-bis(4-[5-acryloyloxypentyloxy]phenylcarbonyloxy) naphthalene;
1,4-bis(4-[6-acryloyloxyhexyloxy]phenylcarbonyloxy) naphthalene;
1,4-bis(4-[7-acryloyloxyheptyloxy]phenylcarbonyloxy) naphthalene;
1,4-bis(4-[9-acryloyloxynonyloxy]phenylcarbonyloxy) naphthalene;
1,4-bis(4-[10-acryloyloxydecyloxy]phenylcarbonyloxy) naphthalene;
1,4-bis(4-[11-acryloyloxyundecyloxy]phenylcarbonyloxy) naphthalene; m.p. (C—I) 106° C., cl.p. (N—I) 98° C.;
1,4-bis(4-[12-acryloyloxydodecyloxy]phenylcarbonyloxy) naphthalene;
1,5-bis(4-[3-acryloyloxypropyloxy]phenylcarbonyloxy) naphthalene;
1,5-bis(4-[4-acryloyloxybutyloxy]phenylcarbonyloxy) naphthalene;
1,5-bis(4-[5-acryloyloxypentyloxy]phenylcarbonyloxy) naphthalene;
1,5-bis(4-[6-acryloyloxyhexyloxy]phenylcarbonyloxy) naphthalene;
1,5-bis(4-[7-acryloyloxyheptyloxy]phenylcarbonyloxy) naphthalene;
1,5-bis(4-[8-acryloyloxyoctyloxy]phenylcarbonyloxy) naphthalene; m.p. (C—I) 130° C., cl.p. (N—I) 108° C.;
1,5-bis(4-[9-acryloyloxynonyloxy]phenylcarbonyloxy) naphthalene;
1,5-bis(4-[10-acryloyloxydecyloxy]phenylcarbonyloxy) naphthalene;
1,5-bis(4-[11-acryloyloxyundecyloxy]phenylcarbonyloxy) naphthalene;
1,5-bis(4-[12-acryloyloxydodecyloxy]phenylcarbonyloxy) naphthalene.

EXAMPLE 2

0.8 g of N,N'-dicyclohexylcarbodiimide is added at room temperature while stirring to a solution of 1.25 g of 4-[8-vinyloxyoctyloxy)]benzoic acid, 0.25 g of 1,4-napththohydroquinone and 0.2 g of 4-dimethylaminopyridine in 20 ml of dichloromethane. The reaction mixture is stirred at room temperature overnight, poured into 100 ml of water and then extracted three times with 50 ml of dichloromethane each time. The organic phases are combined, washed twice with 100 ml of water each time, dried over magnesium sulfate, filtered and the filtrate is subsequently concentrated. Chromatographic purification of the residue on silica gel with cyclohexane/ethyl acetate (vol. 8:2) and two-fold recrystallization from ethyl alcohol of the fractions which are pure according to thin-layer chromatography gives 0.5 g of 1,4-bis(4-[8-vinyloxyoctyloxy]phenylcarbonyloxy)naphthalene.

The following compounds can be prepared in an analogous manner:

1,4-Bis(4-[3-vinyloxypropyloxy]phenylcarbonyloxy) naphthalene;
1,4-bis(4-[4-vinyloxybutyloxy]phenylcarbonyloxy) naphthalene;
1,4-bis(4-[5-vinyloxypentyloxy]phenylcarbonyloxy) naphthalene;
1,4-bis(4-[6-vinyloxyhexyloxy]phenylcarbonyloxy) naphthalene;
1,4-bis(4-[7-vinyloxyheptyloxy]phenylcarbonyloxy) naphthalene;
1,4-bis(4-[9-vinyloxynonyloxy]phenylcarbonyloxy) naphthalene;
1,4-bis(4-[10-vinyloxydecyloxy]phenylcarbonyloxy) naphthalene;
1,4-bis(4-[11-vinyloxyundecyloxy]phenylcarbonyloxy) naphthalene;
1,4-bis(4-[12-vinyloxydodecyloxy]phenylcarbonyloxy) naphthalene;
1,5-bis(4-[3-vinyloxypropyloxy]phenylcarbonyloxy) naphthalene;
1,5-bis(4-[4-vinyloxybutyloxy]phenylcarbonyloxy) naphthalene;
1,5-bis(4-[5-vinyloxypentyloxy]phenylcarbonyloxy) naphthalene;
1,5-bis(4-[6-vinyloxyhexyloxy]phenylcarbonyloxy) naphthalene;
1,5-bis(4-[7-vinyloxyheptyloxy]phenylcarbonyloxy) naphthalene;
1,5-bis(4-[8-vinyloxyoctyloxy]phenylcarbonyloxy) naphthalene;
1,5-bis(4-[9-vinyloxynonyloxy]phenylcarbonyloxy) naphthalene;
1,5-bis(4-[10-vinyloxydecyloxy]phenylcarbonyloxy) naphthalene;
1,5-bis(4-[11-vinyloxyundecyloxy]phenylcarbonyloxy) naphthalene;
1,5-bis(4-[12-vinyloxydodecyloxy]phenylcarbonyloxy) naphthalene.

EXAMPLE 3

0.8 g of N,N'-dicyclohexylcarbodiimide is added at room temperature while stirring to a solution of 1.25 g of 4-[7,8-oxiranoctyloxy)]benzoic acid, 0.25 g of 1,4-naphthohydroquinone and 0.2 g of 4-dimethylaminopyridine in 20 ml of dichloromethane. The reaction mixture is stirred at room temperature overnight, poured into 100 ml of water and then extracted three times with 50 ml of dichloromethane each time. The combined organic phases are washed twice with 100 ml of water each time, dried over magnesium sulphate, filtered and the filtrate is subsequently concentrated. Chromatographic purification of the residue on silica gel with cyclohexane/ethyl acetate (vol. 8:2) and two-fold recrystallization from ethyl alcohol of the fractions which are pure according to thin-layer chromatography gives 0.5 g of 1,4-bis(4-[7,8-oxiranoctyloxy]phenylcarbonyloxy)naphthalene.

The following compounds can be prepared in an analogous manner:

1,4-Bis(4-[2,3-oxiranpropyloxy]phenylcarbonyloxy) naphthalene;
1,4-bis(4-[3,4-oxiranbutyloxy]phenylcarbonyloxy) naphthalene;
1,4-bis(4-[4,5 -oxiranpentyloxy]phenylcarbonyloxy) naphthalene;
1,4-bis(4-[5,6-oxiranhexyloxy]phenylcarbonyloxy) naphthalene;
1,4-bis(4-[6,7-oxiranheptyloxy]phenylcarbonyloxy) naphthalene;
1,4-bis(4-[8,9-oxirannonyloxy]phenylcarbonyloxy) naphthalene;
1,4-bis(4-[9,10-oxirandecyloxy]phenylcarbonyloxy) naphthalene;
1,4-bis(4-[10,11-oxiranundecyloxy]phenylcarbonyloxy) naphthalene;
1,4-bis(4-[11,12-oxirandodecyloxy]phenylcarbonyloxy) naphthalene;
1,5-bis(4-[2,3-oxiranpropyloxy]phenylcarbonyloxy) naphthalene;
1,5-bis(4-[3,4-oxiranbutyloxy]phenylcarbonyloxy) naphthalene;
1,5-bis(4-[4,5-oxiranpentyloxy]phenylcarbonyloxy) naphthalene;
1,5-bis(4-[5,6-oxiranhexyloxy]phenylcarbonyloxy) naphthalene;
1,5-bis(4-[6,7-oxiranheptyloxy]phenylcarbonyloxy) naphthalene;
1,5-bis(4-[7,8-oxiranoctyloxy]phenylcarbonyloxy) naphthalene;
1,5-bis(4-[8,9-oxirannonyloxy]phenylcarbonyloxy) naphthalene;
1,5-bis(4-[9,10-oxirandecyloxy]phenylcarbonyloxy) naphthalene;
1,5-bis(4-[10,11-oxiranundecyloxy]phenylcarbonyloxy) naphthalene;
1,5-bis(4-[11,12-oxirandodecyloxy]phenylcarbonyloxy) naphthalene.

EXAMPLE 4

A mixture (C—N, <20° C., N—I, 105 ° C.) of 80 wt. % 1,4-bis(4-[8-acryloyloxyoctyloxy]phenylcarbonyloxy) naphthalene and 20 wt. % 1-chloro-2,5-bis(4-[6-acryloyloxyhexyloxy)]phenylcarbonyloxy)benzene was provided, treated with 1 wt. % of a photoinitiator (IRGACURE, Ciba Geigy), dissolved in anisole (40 wt. %) and then spun on to a glass plate at 2000 revolutions per minute. The glass plate had previously been coated with poly [methacryloyloxyethyl 3-(E)-[4-cyano-4'-biphenyl] acrylate] and then irradiated with linear polarized light as described in the Swiss Patent Application CH 2016/94. Thereby, a predetermined structure was inscribed photolithographically by means of a mask in the (PPN) layer. The new layer (on the PPN layer) was dried at 90° C. on a heating block, then irradiated with xenon light in a vacuum oven under a vacuum at 90° C. The inscribed original structure remained and was copied faithfully by the new network. A clear double refraction (Δv) was recognizable. This layer can be used as a structured optical retarder.

The subject invention has been described in terms of its preferred embodiments. Upon reading the present purification certain alternative embodiments will become obvious to those skilled in the art. These variations, such as the choice of cross-linkable group, are to be considered within the scope and spirit of the present invention which is only to be limited by the claims which follow and their equivalents.

What is claimed is:

1. A compound of the formula:

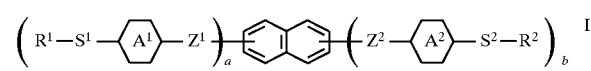

wherein $R^1$ and $R^2$ each independently is a cross-linkable group;
$S^1$ and $S^2$ each independently is —$(CY_2)_m$—, —$O(CY_2)_m$—, —$(CY_2)_mO$—, —$(CY_2)_mCOO$—, —$(CY_2)_mOOC$—, —$(Si[(CH_3)_2]O)_m$—, —$OCH_2(Si[(CH_3)_2]O)_mSi[(CH_3)_2]CH_2O$—, or —$NHCH_2(Si[(CH_3)_2]O)_mSi[(CH_3)_2]CH_2NH$—;
Y is hydrogen, fluorine, or methyl;
a is 0 or 1;
b is 1 or 2, and a+b=2;
m is a whole number of from 1 to 16;
$A^1$ and $A^2$ each independently is pyridine-2,5-diyl, pyrimidine-2,5-diyl, trans-1,4-cyclohexylene, trans-1,3-dioxane-2,5-diyl, or 1,4-phenylene which is unsubstituted, mono-substituted or multiply-substituted with one or more substituents selected from the group consisting of halogen, cyano, methyl, methoxy, and acetyl; and
$Z^1$ and $Z^2$ each independently is a single bond, —$CH_2CH_2$—, —$OCH_2$—, —$CH_2O$—, —$COO$—, —$OOC$—, —$(CH_2)_4$—, —$O(CH_2)_3$—, or —$(CH_2)_3O$—.

2. The compound of claim 1, wherein the cross-linkable group is selected from the group consisting of ethylene, acrylate, methacrylate, 2-chloroacrylate, 2-phenylacrylate, acryloylphenylene, acrylamide, methacrylamide, 2-chloroacrylamide, 2-phenylacrylamide, epoxy, itaconic acid ester, vinyloxy, vinyl ester, styrene derivative, siloxane, ethyleneimine derivative, maleic acid derivative, fumaric acid derivative, and a cinnamic acid derivative which is unsubsituted, mono-substituted, or multiply-substituted with one or more substituents selected from the group consisting of methyl, methoxy, cyano, and halogen.

3. The compound according to claim 1, wherein the naphthyl ring is linked in position 1 and 5, or in position 1 and 4, with $Z^1$ and $Z^2$.

4. The compound according to claim 1, wherein $R^1$ and $R^2$ are the same.

5. The compound according to claim 2, wherein $R^1$ and $R^2$ are the same.

6. The compound according to claim 3, wherein $R^1$ and $R^2$ are the same.

7. The compound according to claim 1, wherein $R^1$ and $R^2$ are selected from the group consisting of acrylate, methacrylate, 2-chloroacrylate, 2-phenylacrylate, vinyloxy, and epoxy.

8. The compound according to claim 2, wherein $R^1$ and $R^2$ are selected from the group consisting of acrylate, methacrylate, 2-chloroacrylate, 2-phenylacrylate, vinyloxy, and epoxy.

9. The compound according to claim 3, wherein $R^1$ and $R^2$ are selected from the group consisting of acrylate, methacrylate, 2-chloroacrylate, 2-phenylacrylate, vinyloxy, and epoxy.

10. The compound according to claim 4, wherein $R^1$ and $R^2$ are selected from the group consisting of acrylate, methacrylate, 2-chloroacrylate, 2-phenylacrylate, vinyloxy, and epoxy.

11. The compound according to claim 5, wherein $R^1$ and $R^2$ are selected from the group consisting of acrylate, methacrylate, 2-chloroacrylate, 2-phenylacrylate, vinyloxy, and epoxy.

12. The compound according to claim 6, wherein $R^1$ and $R^2$ are selected from the group consisting of acrylate, methacrylate, 2-chloroacrylate, 2-phenylacrylate, vinyloxy, and epoxy.

13. The compound according to claim 1, wherein $S^1$ and $S^2$ are the same.

14. The compound according to claim 2, wherein $S^1$ and $S^2$ are the same.

15. The compound according to claim 3, wherein $S^1$ and $S^2$ are the same.

16. The compound according to claim 4, wherein $S^1$ and $S^2$ are the same.

17. The compound according to claim 5, wherein $S^1$ and $S^2$ are the same.

18. The compound according to claim 6, wherein $S^1$ and $S^2$ are the same.

19. The compound according to claim 7, wherein $S^1$ and $S^2$ are the same.

20. The compound according to claim 8, wherein $S^1$ and $S^2$ are the same.

21. The compound according to claims 1, wherein $Z^1$ and $Z^2$ are the same and are selected from the group consisting of —OCH$_2$—, —CH$_2$O—, —COO—, and —OOC—.

22. The compound according to claims 2, wherein $Z^1$ and $Z^2$ are the same and are selected from the group consisting of —OCH$_2$—, —CH$_2$O—, —COO—, and —OOC—.

23. The compound according to claims 3, wherein $Z^1$ and $Z^2$ are the same and are selected from the group consisting of —OCH$_2$—, —CH$_2$O—, —COO—, and —OOC—.

24. The compound according to claim 1, wherein rings $A^1$ and $A^2$ are the same and are selected from the group consisting of 1,4-phenylene, 2-fluoro-1,4-phenylene, and 3-fluoro-1,4-phenylene.

25. The compound according to claim 2, wherein rings $A^1$ and $A^2$ are the same and are selected from the group consisting of 1,4-phenylene, 2-fluoro-1,4-phenylene, and 3-fluoro-1,4-phenylene.

26. The compound according to claim 3, wherein rings $A^1$ and $A^2$ are the same and are selected from the group consisting of 1,4-phenylene, 2-fluoro-1,4-phenylene, and 3-fluoro-1,4-phenylene.

27. The compound according to claim 1 of the formula:

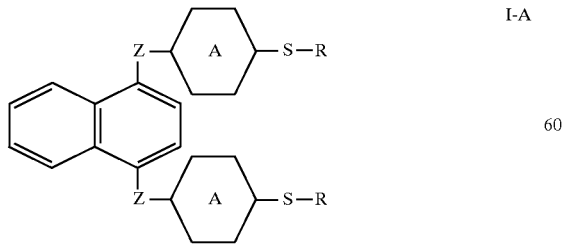

I-A wherein

R is acrylate, methacrylate, 2-chloroacrylate, 2-phenylacrylate, vinyloxy, or epoxy;

S is —(CH$_2$)$_{m'}$—, —O(CH$_2$)$_{m'}$—, or —(CH$_2$)$_{m'}$O—;

m' is a whole number of from 4 to 12;

A is 1,4-phenylene, 2-fluoro-1,4-phenylene, or 3-fluoro-1,4-phenylene; and

Z is —OCH$_2$— or —OOC—.

28. The compound according to claim 1 of the formula:

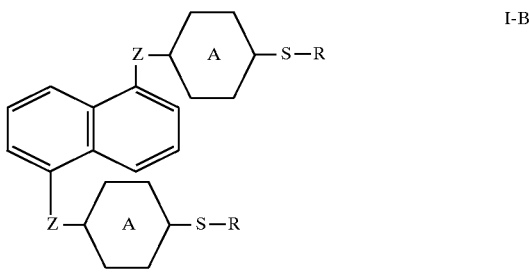

I-B wherein

R is acrylate, methacrylate, 2-chloroacrylate, 2-phenylacrylate, vinyloxy, or epoxy;

S is —(CH$_2$)$_{m'}$—, —O(CH$_2$)$_{m'}$—, or —(CH$_2$)$_{m'}$O—;

m' is a whole number of from 4 to 12;

A is 1,4-phenylene, 2-fluoro-1,4-phenylene, or 3-fluoro-1,4-phenylene; and

Z is —OCH$_2$— or —OOC—.

29. A cross-linkable mixture consisting of at least 2 components, of which at least one component is a compound of formula I

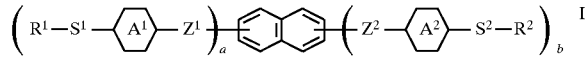

I wherein $R^1$ and $R^2$ each independently is a cross-linkable group;

$S^1$ and $S^2$ each independently is —(CY$_2$)$_m$—, —O(CY$_2$)$_m$—, —(CY$_2$)$_m$O—, —(CY$_2$)$_m$COO—, —(CY$_2$)$_m$OOC—, —(Si[(CH$_3$)$_2$]O)$_m$—, —OCH$_2$(Si[(CH$_3$)$_2$]O)$_m$Si[(CH$_3$)$_2$]CH$_2$O—, or —NHCH$_2$(Si[(CH$_3$)$_2$]O)$_m$Si[(CH$_3$)$_2$]CH$_2$NH—;

Y is hydrogen, fluorine, or methyl;

a is 0 or 1;

b is 1 or 2, and a+b=2;

m is a whole number of from 1 to 16;

$A^1$ and $A^2$ each independently is pyridine-2,5-diyl, pyrimidine-2,5-diyl, trans-1,4-cyclohexylene, trans-1,3-dioxane-2,5-diyl, or 1,4-phenylene which is unsubstituted, mono-substituted, or multiply-substituted with one or more substituents selected from the group consisting of halogen, cyano, methyl, methoxy, and acetyl; and $Z^1$ and $Z^2$ each independently is a single bond, —CH$_2$CH$_2$—, —OCH$_2$—, —CH$_2$O—, —COO—, —OOC—, —(CH$_2$)$_4$—, —O(CH$_2$)$_3$—, or —(CH$_2$)$_3$O—.

30. The cross-linkable mixture according to claim 29 further comprising one or more compounds selected from the group consisting of:

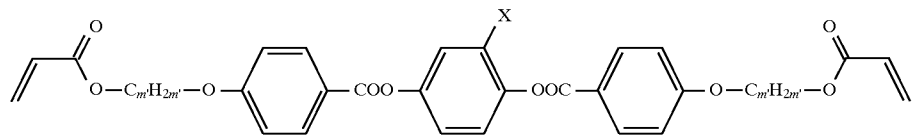
II
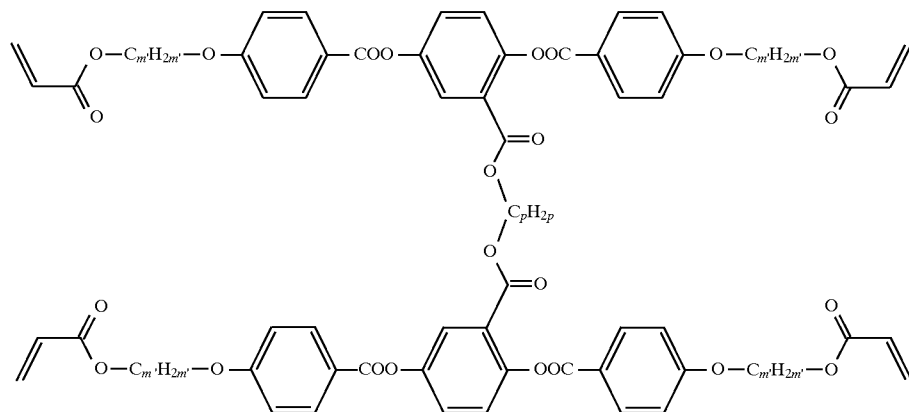
III
IV
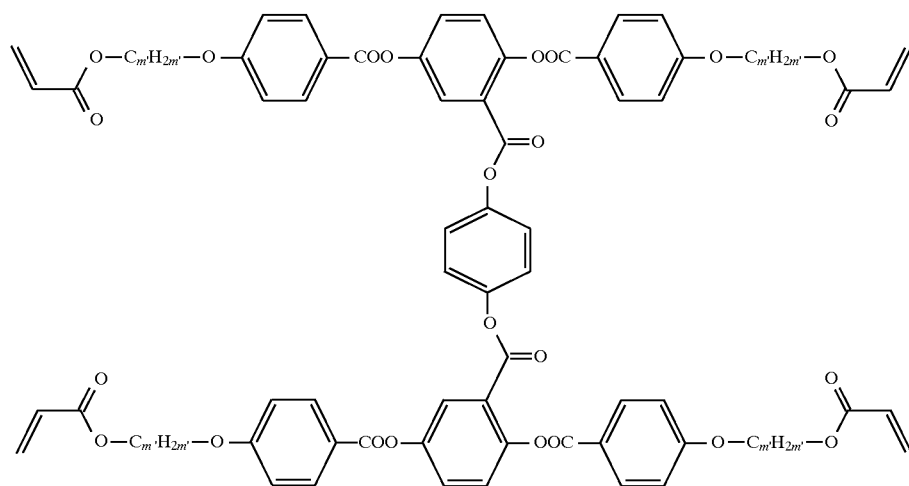
V
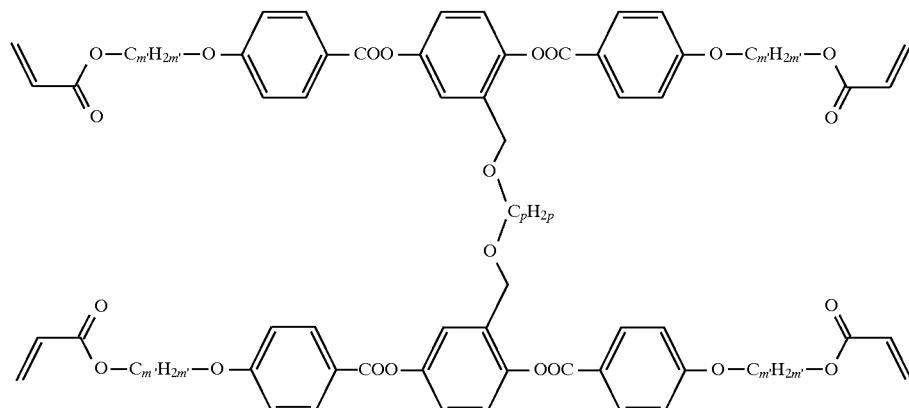

-continued
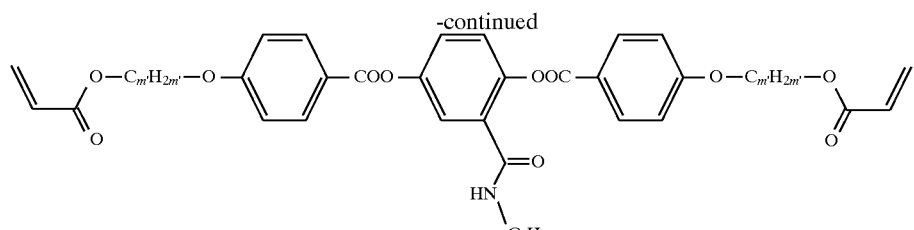
VI
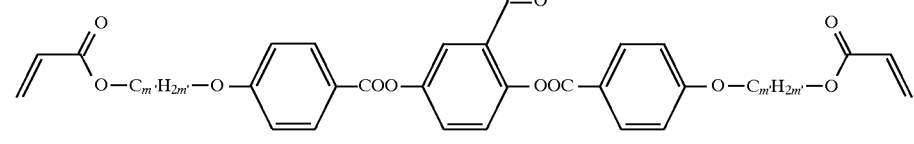
VII
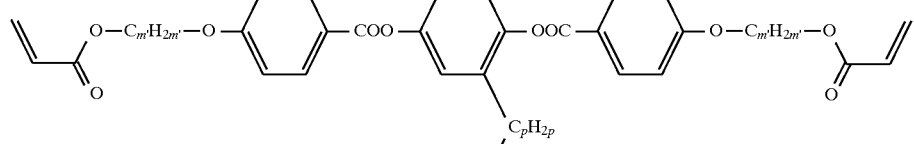
VIII
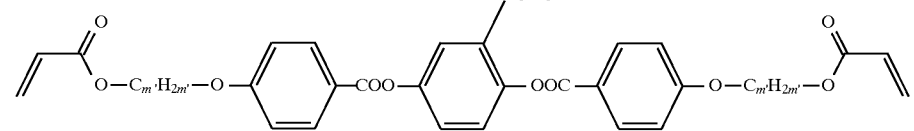
IX
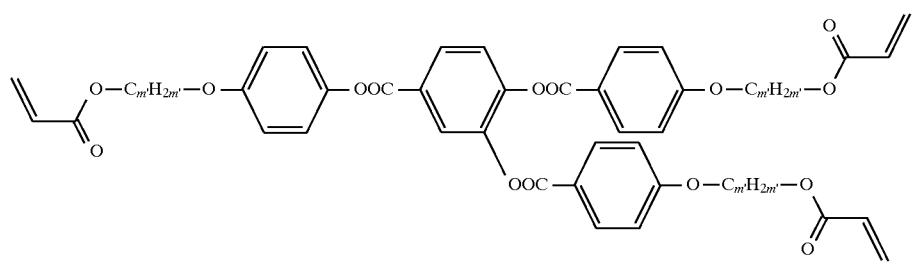
X
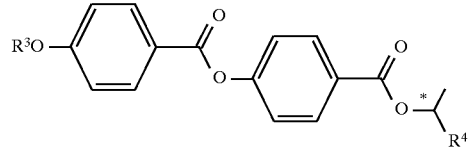
XI
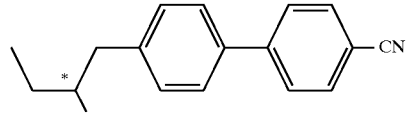
and
XII
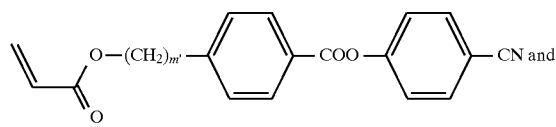
wherein
p signifies a whole number of 2 to 12;
$R^3$ and $R^4$ each independently signify alkyl or alkenyl with 2 to 12 carbon atoms;
X signifies hydrogen, lower alkyl, fluorine, bromine, chlorine or cyano;
m' signifies a whole number of 4 to 12; and
* signifies a center of chirality.
* * * * *